United States Patent

Ando et al.

[11] Patent Number: 5,534,522
[45] Date of Patent: Jul. 9, 1996

[54] (R)-(Z)-1-AZABICYCLO [2.2.1] HEPTAN-3-ONE,O-[3-(3-METHOXYPHENYL)-2-PROPYNYL] OXIME MALEATE AS A PHARMACEUTICAL AGENT

[75] Inventors: Howard Y. Ando, Ypsilanti; Stephen D. Barrett, Livonia; Juan C. Jaen, Plymouth; Steven E. Rose; Haile Tecle, both of Ann Arbor, all of Mich.

[73] Assignee: Warner-Lambert Company, Morris Plains, N.J.

[21] Appl. No.: 474,622

[22] Filed: Jun. 7, 1995

[51] Int. Cl.⁶ .................................................. A61K 31/445
[52] U.S. Cl. .......................................... 514/299; 546/112
[58] Field of Search ............................ 514/299; 546/112

[56] References Cited

U.S. PATENT DOCUMENTS 5,306,718  4/1994  Lauffer et al. ..................... 514/230.8
5,346,911  9/1994  Augelli-Szafran et al. ............ 514/339

*Primary Examiner*—Peter O'Sullivan
*Attorney, Agent, or Firm*—Elizabeth M. Anderson

[57] ABSTRACT

The [1:1] maleate salt of [R-(Z)]-1-Azabicyclo [2.2.1]heptan-3-one, O-[3-(3-methoxyphenyl)-2-propynyl]-oxime, a known muscarinic agonist has unique properties relative to other salts of the compound, rendering it a desirable pharmaceutical.

6 Claims, 4 Drawing Sheets

FIG. 1 HPLC Analysis of Sample Containing 1a Maleate and 1c Maleate

FIG. 2  Ethyl Acetate Recrystallized Particles (scale units 10 μm)

FIG. 3  Ether-Precipitated Particles (scale units 10 μm)

(R)-(Z)-1-AZABICYCLO [2.2.1] HEPTAN-3-ONE,O-[3-(3-METHOXYPHENYL)-2-PROPYNYL] OXIME MALEATE AS A PHARMACEUTICAL AGENT

BACKGROUND OF THE INVENTION

The instant invention is a crystalline salt of (R)-(Z)-1-Azabicyclo[2.2.1]heptan-3-one,O-[3-(3-methoxyphenyl)-2-propynyl]oxime, and maleic acid (1:1 ratio) (the compound) which provides a pharmaceutical form with properties superior to the free base or any of the other pharmaceutically acceptable salt forms of this compound.

The chemical structure of this salt is

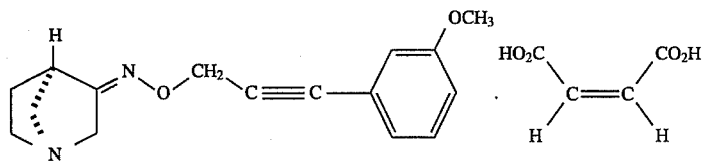

Compounds of Formula I below, and more specifically a subset of compounds of Formula II below, are covered in U.S. Pat. No. 5,306,718 and its continuation-in-part U.S. Pat. No. 5,346,911 as muscarinic agonists, useful agents for the treatment of pain and cognitive decline associated with brain cholinergic deficiency, such as Alzheimer's disease.

Compounds of Formula II where Ar is a phenyl group substituted by one or two methoxy groups possess some of the most interesting profiles of pharmacological activity in vitro (Jaen, et al., *Life Sciences*, 1995;56:845–852 (Table I of the reference)). One of these compounds in particular (1), which contains a (3-methoxyphenyl)propargyl oxime side chain, was identified in this and earlier publications (Davis R., et al., *Prog. Brain Res.*, 1993;98:439–445) as displaying a very favorable overall profile of pharmacological activity, as illustrated by its high affinity to rat cerebral cortex muscarinic receptors, the ability to displace an agonist radiolabeled ligand (cis-methyldioxolane) from muscarinic receptors at 246 times lower concentrations than those required to displace an antagonist radioligand (quinuclidinyl benzilate), and its ability to selectively stimulate m1-subtype muscarinic receptors without significant stimulation of other non-m1 muscarinic receptors.

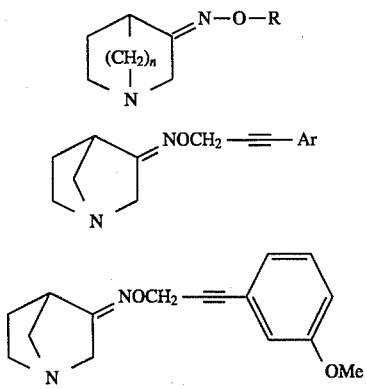

A compound with the chemical structure of 1 above may exist as any of four stereochemical isomers, represented by 1a, 1b, 1c, and 1d below.

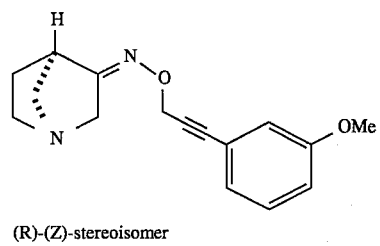

(R)-(Z)-stereoisomer    1a

-continued

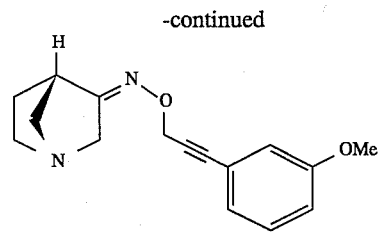

(S)-(Z)-stereoisomer    1b

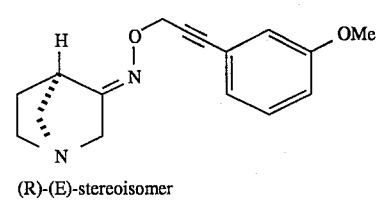

(R)-(E)-stereoisomer    1c

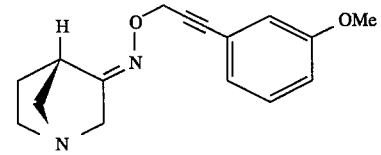

(S)-(E)-stereoisomer    1d

Isomers 1a and 1b are enantiomers (i.e., mirror images of each other), the same being true for isomers 1c and 1d. Since the asymmetric center of these molecules is on a bridgehead carbon, which cannot epimerize under any normal conditions, resolution of these enantiomeric pairs (that is, separation of 1a from 1b or separation of 1c from 1d) can be accomplished by synthetic or resolution techniques described in U.S. Pat. No. 5,346,911 and is permanent. This means, for example, that 1a cannot interconvert to its enantiomer 1b and 1c cannot interconvert to 1d. On the other hand, 1a and 1c possess the same absolute stereochemistry at the bridgehead carbon atom but are geometric isomers of each other at the oxime carbon-nitrogen double bond. The same relationship exists between isomers 1b and 1d.

The muscarinic agonist efficacy of oxime 1 resides primarily in isomer 1a (Jaen ibid and Table I below). Tables II and III of the reference indicate that isomer 1a (designated R-8 in the Jaen reference) displays greater m1 receptor subtype selectivity and greater m1 potency than isomer 1b (designated S-8). The small amount of activity displayed by 1b could be due to the presence of small amounts of 1a in the samples of 1b. A comparison between 1a and a mixture of 1c/1d, shown in Table I below, indicates that 1a is more potent and more efficacious as a muscarinic agonist (as determined by the greater ratio of quinuclidinyl benzilate (QNB) to cis-methyldioxolane (CMD) binding for 1a). As a result of these and other experiments, 1a was identified as an optimal compound (high efficacy muscarinic agonist with high selectivity for m1 muscarinic receptor subtypes) for development as a treatment for cognitive malfunction associated with cholinergic deficits, such as Alzheimer's disease.

TABLE I

| Compound | Muscarinic Receptor Binding | |
| --- | --- | --- |
|  | CMD Binding $IC_{50}$ (nM) | QNB Binding $IC_{50}$ (nM) |
| 1a | 25 | 5300 |
| (1c + 1d)[a] | 150 | 14800 |

[a]Racemic (E)-oxime was used in these assays.

Some oxime carbon-nitrogen double bonds are relatively stable, while others can undergo facile rearrangement, typically in the presence of acid catalysts. The specific substitution pattern around the oxime moiety typically determines the chemical stability of the oxime (propensity to hydrolyze into its ketone and hydroxylamine components), its stereochemical integrity (the tendency of each geometric isomer to remain in the E or Z configuration), and the exact position of the thermodynamic equilibrium between both stereochemical forms (when chemical conditions are such that an equilibrium can be reached). As shown in Table II below, Compound 1a can undergo acid-catalyzed isomerization to produce its geometric isomer 1c. This equilibration is time- and pH-dependent. We have determined that the thermodynamic equilibrium ratio of 1a:1c in solution is approximately 85:15.

TABLE II

| Z:E Peak Area Ratios as a Function of pH After 24 Hours Incubation of 1a at 37° C. | |
| --- | --- |
| pH | Peak-Area Ratio (1a:1c) |
| 0.1 N HCl | 85:15 |
| pH 1.97 | 88:12 |
| pH 4.03 | 99.3:0.7 |
| >4.03 | 100:0 |

There are multiple reasons for not considering an 85:15 mixture of these two isomers as an optimal entity for development as a pharmaceutical drug: The 85:15 ratio of isomers is not always produced in exactly equal amounts from batch to batch, interpretation of the pharmacology, toxicity, and clinical efficacy of such a mixture would be much more difficult than when dealing with a single compound, and the cost of developing a fixed mixture as a clinically useful drug would also be significantly higher; and finally, the physical properties of an 85:15 combination of isomers are less optimal than those of pure 1a in terms of crystallinity, physical, and chemical stability.

The development of 1a as a pharmaceutical drug required the identification of a salt form or free base of 1a with optimal physical and chemical properties. The most critical properties included: Easy and reproducible preparation, crystallinity, non-hygroscopicity, aqueous solubility, stability to visible and ultraviolet light, low rate of degradation under accelerated stability conditions of temperature and humidity, low rate of isomerization of 1a to its isomer 1c under these conditions, and safety for long-term administration to humans.

The free base and certain pharmaceutically acceptable salts are covered in U.S. Pat. No. 5,306,718 and continuation-in-part U.S. Pat. No. 5,346,911. The salts listed are: hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane and ethanesulfonic, hydroxymethane- and hydroxyethanesulfonic. There is no teaching or suggestion that the maleate is a superior salt form of the above structure. Clearly the excellent properties of the maleate salt were not known or appreciated until now.

These two patents are hereby incorporated by reference. We have discovered that not all of the salts are equally useful, as judged by the list of properties described above. In particular, we have discovered the unexpected excellent properties of the maleic acid salt (1:1) of 1a, which clearly distinguishes this salt.

SUMMARY OF THE INVENTION

Of the large number of salts of Compound 1a prepared and examined, quite unexpectedly, only the maleate [1:1] salt satisfied all of the inventors' standards as a pharmaceutically acceptable and desirable salt: ease of preparation without isomerization, consistent and reproducible stoichiometry, crystallinity, aqueous solubility, light stability, non-hygroscopicity, non-toxicity, and general physical and chemical stability. The present invention is, therefore, directed to the [1:1] salt of Compound 1a with maleic acid, its preparation in such a way that large particle size crystals of the salt are obtained, and the method of use of this salt to treat cognitive deficits and pain. The chemical name of this salt is (R)-(Z)-1-azabicyclo[2.2.1]heptan-3-one,O-[3-(3-methoxyphenyl)-2-propynyl]oxime, (Z)-butenedioic acid, [1:1 salt]. The majority of crystal particles are greater than 10×10 µm in size; at least half of the particles are larger than 10×10 µm.

DETAILED DESCRIPTION

Figure 1:
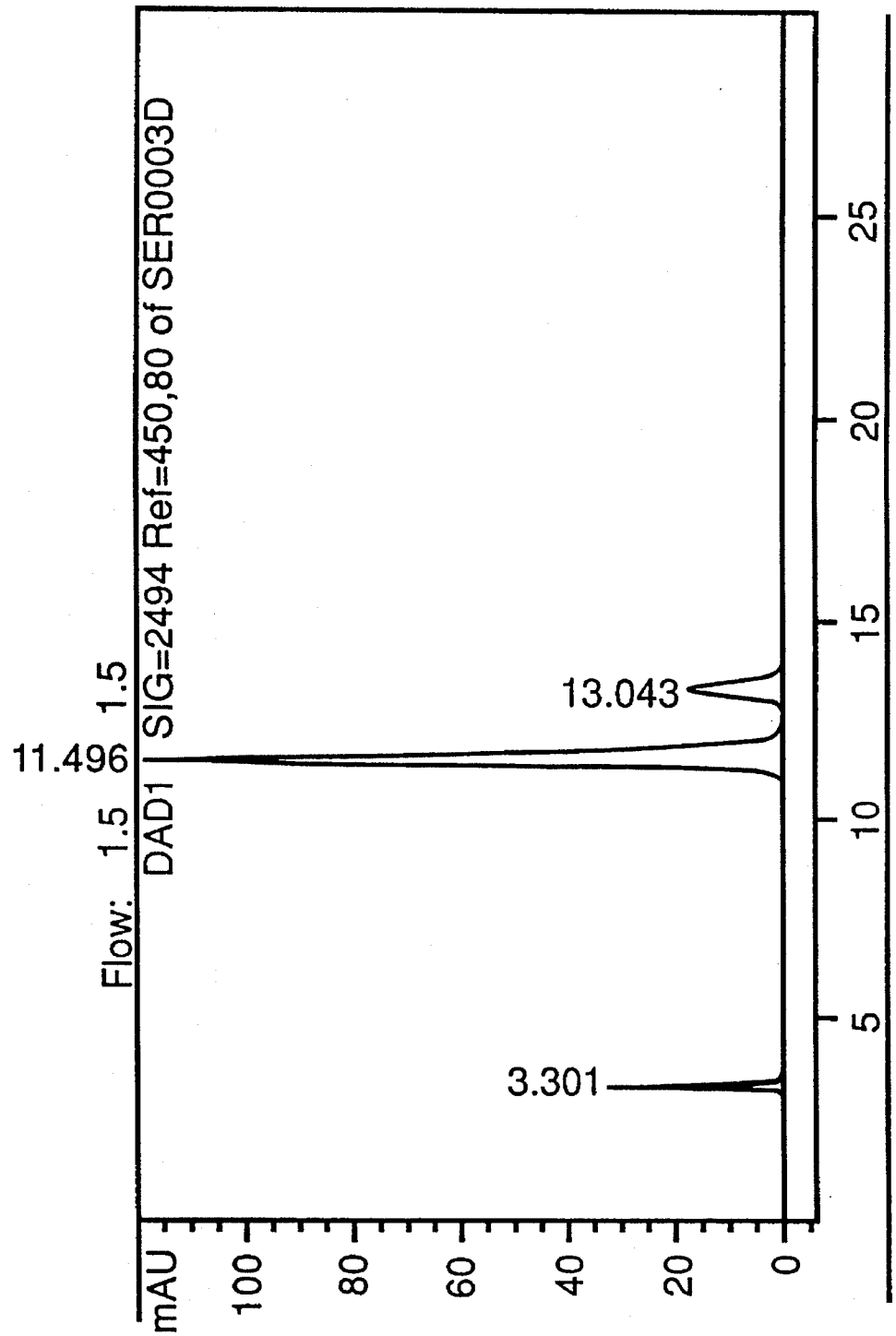
FIG. 1 shows the separation of 1a and 1c by HPLC.

The salt selection process for the muscarinic agonist of the instant invention revolved around issues key to pharmaceutical compounds.

The most critical properties included: Easy and reproducible preparation, crystallinity, non-hygroscopicity, aqueous solubility, stability to visible and ultraviolet light, low rate of degradation under accelerated stability conditions of temperature and humidity, low rate of isomerization of 1a to its isomer 1c under these conditions, and safety for long-term administration to humans.

Many counter-ions were evaluated for salt-forming properties. See Table III below. The data presented in Table III answer the following questions: (1) did a solid salt precipitate from ether when free base 1a was treated with each acid?; (2) following collection of the salt by either filtration or evaporation of the ether, what solvents were used to crystallize the salt, and was a crystalline salt obtained from each solvent?; (3) melting point information; and (4) overall rating of each salt, based on considerations of ease of formation and crystallinity.

TABLE III

Evaluation of Acid Addition Salts of (R)-(Z)-1azabicyclo[2.2.1]heptan-3-one, O-[3-(3-methoxyphenyl)-2-propynyl]oxime

| Acid Anion | Results: PPT From Ether | Recrystallization Solvent | | Results | Melting Point | Overall Salt Rating |
|---|---|---|---|---|---|---|
| Inorganic | | | | | | |
| 1. Hydrobromide | Yes | 1. Et$_2$O | Precipitation | Amorphous Solid (very hygroscopic) | — | Low |
| 2. Hydrochloride | Yes | 1. Et$_2$O | Precipitation | White Solid | 158–160 | High |
| | | 2. EtOAc | Recystallization | White Solid E-Isomer Formation | 159–160 | |
| Monocarboxylic | | | | | | |
| 3. Acetate | No | 1. Et$_2$O | Evaporation | Oil | — | Low |
| | | 2. Pet Ether | Trituration | Oil | | |
| | | 3. IPA/Pet Ether | Crystallization | Oil | | |
| 4. Benzoate | No | 1. Et$_2$O | Evaporation | Oil | | High |
| | | 2. Pentane | Trituration | White Crystals | 86–88 | |
| | | 3. t-Butylmethylether | Crystallization | White Crystals | 88–89 | |
| 5. n-Butyrate$^a$ | No | 1. Et$_2$O | Evaporation | Oil | — | Low |
| | | 2. Pentane | Trituration | Oil | | |
| 6. tert-Butyrate$^a$ | No | 1. Et$_2$O | Evaporation | Oil | — | Low |
| | | 2. Pentane | Trituration | Oil | | |
| 7. L(+)-Lactate | No (MeOH) | 1. MeOH | Evaporation | Oil | — | Low |
| | | 2. Pentane | Trituration | Oil | | |
| 8. 1-Naphthoate | No | 1. Et$_2$O | Evaporation | Oil | — | Low |
| | | 2. Pentane | Trituration | Oil | | |
| 9. 2-Naphthoate | No | 1. Et$_2$O | Evaporation | Gum | — | Low |
| | | 2. Pentane | Trituration | Gum | | |
| Monocarboxylic (cont) | | | | | | |
| 9. 2-Naphthoate (cont) | | 3. Toluene | Cyrstallization | No PPT | | |
| | | 4. Acetone | Crystallization | No PPT | | |
| | | 5. t-Butylmethylether | Crystallization | No PPT | | |
| | | 6. Cyclohexane | Crystallization | Solid = 2-Naphthoic Acid | | |
| 10. Propionate | No | 1. Et$_2$O | Evaporation | Oil | — | Low |
| | | 2. Pentane | Trituration | Oil | | |
| 11. Stearate | No | 1. Et$_2$O | Crystallization | Solid = Stearic acid | — | Low |
| 12. Undecanoate | No | 1. Et$_2$O | Evaporation | Oil | — | Low |
| Polycarboxylic | | | | | | |
| 13. Citrate | Yes | 1. Et$_2$O | Precipitation | White Amorphous Solid | 53–54 | Medium |
| 14. Fumarate (0.5 epui) | No (MeOH) | 1. MeOH | Evaporation | Gum | | Medium |
| | | 2. EtOAc | Trituration | Solid | 79–109 | |
| | | 3. EtOAc:Pentane (1:1) | Trituration | Solid | 106–108 | |
| | | 4. EtOAc | Crystallization | Gum | | |
| | | 5. EtOH/Pentane | Crystallization | No PPT | | |
| | | 6. IPA/Pentane | Crystallization | No PPT | | |
| | | 7. EtOH | Crystallization | No PPT | | |
| | | 8. IPA | Crystallization | No PPT | | |
| | | 9. Cyclohexane/CHCl$_3$ | Crystallization | | | |
| 15. Fumarate (1 equi) | Yes | 1. Et$_2$O | Precipitation | Amorphous Solid | | Low |
| | | 2. EtOH/Pentane | Crystallization | Oil | | |
| Polycarboxylic (cont) | | | | | | |
| 15. Fumarate (1 equi) | | 3. IPA/Pentane | Recrystallization | Oil | | |
| | | 4. EtOH | Recrystallization | Oil | | |
| | | 5. IPA | Recrystallization | Oil | | |
| | | 6. EtOAc | Recrystallization | Oil | | |
| 16. Maleate | Yes | 1. Et$_2$O | Evaporation | White Crystals | 115–116 | High |
| | | 2. EtOAc | Recrystallization | White Crystals | 118–119 | |
| | | 3. IPA/EtOH/Pentane | Recrystallization | White Crystals | 116.5–118 | |
| | | 4. EtOH/Pentane | Recrystallization | White Crystals | 118.5–121 | |
| | | 5. CHCl$_3$/Pentane | Recrystallization | White Crystals | 118–119.5 | |
| | | 6. EtOH | Recrystallization | White Crystals | 115–118 | |

TABLE III-continued

Evaluation of Acid Addition Salts of (R)-(Z)-1azabicyclo[2.2.1]heptan-3-one, O-[3-(3-methoxyphenyl)-2-propynyl]oxime

| Acid Anion | Results: PPT From Ether | Recrystallization Solvent | | Results | Melting Point | Overall Salt Rating |
|---|---|---|---|---|---|---|
| 17. Malate | Yes | 1. Et$_2$O | Precipitation | White Gum | — | Low |
| | | 3. IPA/EtOH/Pentane | Recrystallization | Oil | | |
| | | 4. EtOH/Pentane | Recrystallization | Oil | | |
| 18. Oxalate | Yes | 1. Et$_2$O | Precipitation | White Solid Inconsistent Stoichiometry | Variable 110–113 for 1:1 Salt | Medium |
| 19. Succinate | No (MeOH) | 1. MeOH | Evaporation | Oil | | Low |
| | | 2. t-Butylmethylether/ Pentane | Crystallization | Oil | | |
| | | 3. Et$_2$O/Pentane | Crystallization | Oil | | |
| 20. Tartrate (L)-(+) (0.5 equi) | No (MeOH) | 1. MeOH | Evaporation | Gum | | Low |
| | | 2. Pentane | Trituration | Sticky Gum | | |
| | | 3. MeOH/Ether | Crystallization | Amorphous White Solid | 58 (Glass) | |
| | | 4. t-Butylmethylether | Crystallization | No PPT | | |
| | | 5. EtOAc | Crystallization | Oily PPT | | |
| | | 6. EtOAc/Pentane | Crystallization | No PPT | | |
| | | 7. EtOH/Pet Ether | Crystallization | No PPT | | |
| Polycarboxylic (cont) | | | | | | |
| 21. Tartrate (L)-(+) (1 equi) | No (MeOH) | 1. MeOH | Evaporation | Oil | — | Low |
| | | 2. EtOH/Pet Ether | Crystallization | No PPT | | |
| 22. Tartrate (D)-(−) (0.5 equi) | No (MeOH) | 1. MeOH | Evaporation | Gum | — | Low |
| | | 2. EtOH/Pet Ether | Crystallization | No PPT | | |
| 23. Tartrate (D)-(−) (1 equi) | No (MeOH) | 1. MeOH | Evaporation | Gum | | Low |
| Sulfonic | | | | | | |
| 24. Benzene Sulfonae Sulphonate | No | 1. Et$_2$O | Evaporation | Oil | — | Low |
| | | 2. Pentane | Trituration | Oil | | |
| Amino Acid | | | | | | |
| 25. N-acetylgly-cinate | No (EtOAc/ MeOH) | 1. EtOAc/MeOH | Evaporation | Oil | — | Low |
| | | 2. Et$_2$O and Pentane | Trituration | | | |
| Other | | | | | | |
| 26. Saccharin | No (MeOH) | 1. MeOH | Evaporation | Oil | — | Low |
| | | 2. Pentane | Trituration | Oil | | |
| | | 3. Ether | Trituration | Oil | | |
| | | 4. t-Butylmethylether | Crystallization | No PPT | | |
| | | 5. Acetone/Pentane | Crystallization | Oily PPT | | |

$^a$Racemic oxime was used.

Of the more than 26 salts examined, only four salts provided reasonably crystalline forms: the hydrochloride, the oxalate, the maleate, and the benzoate.

Table IV below shows the moisture uptake of three of these four salts. The HCl salt took up water most rapidly and to the greatest extent; the maleate the least.

Generally, hygroscopicity is an important but not critical factor in salt selection. Precaution can be taken in manufacturing to deal with a wide variety of variables if necessary. On the other hand, other things being equal, a non-hygroscopic form is highly desirable.

For Compound 1a, the fact that the hydrochloride salt is extremely hygroscopic is of major concern because the uptake of moisture lowers the microenvironmental pH of the solid leading to the formation of 1c, even in the solid state. Prior studies have shown that the conversion of 1a to 1c occurs under low pH conditions. In addition, the hydrochloride form is difficult to recrystallize without converting 1a to 1c.

For pharmaceuticals, higher melting points are more desirable than low, as higher melting point compounds tend to be more stable, both physically and chemically, during pharmaceutical processing. Both the maleate and the hydrochloride salts provided these more desirable characteristics.

The oxalate salt, even though less hygroscopic than the hydrochloride, cannot be prepared with a consistent stoichiometry, thus limiting its potential for development. Additionally, significant concerns exist about the toxicity of long-term administration of oxalic acid to patients (The Merk Index, 10th Edition, Merck & Co., Inc., Rahway, N.J., 1983:6784; and Gosselin R E, et al., Ed. *Clinical Toxicology of Commercial Products*. Williams & Wilkins, Baltimore, 4th Edition, 1976; Section III:260–263).

TABLE IV

| Hygroscopicity of Salts of Compound 1a | | | | |
| --- | --- | --- | --- | --- |
| | Benzoate | Oxalate | Maleate | Hydrochloride |
| Hygroscopicity (% wt ↑)[a] | Not Determined | 6.38 ± 1.40 | 0.32 ± 0.02 | 27.77 ± 0.40 |
| Melting Point (°C.) | 89 (DSC) | 110 | 119 (DSC) | 158 |

[a]Hygroscopicity at RT; 81% RH for 16 days using crimped DSC pans

Effect of Temperature, Relative Humidity, and Light on Crystalline Salts of 1a

Table V below summarizes results of stability studies on the least-hygroscopic crystalline salts of 1a. The maleate and benzoate salts were studied in the most detail. No temperature/humidity discrimination occurred with the accelerated condition, 30° C./60% RH after 2 weeks; the maleate and benzoate were both stable at 25° C./60% RH and 30° C./60% RH.

TABLE V

| Stability of Crystalline Salts of 1a Under Accelerated Stability Conditions | | | |
| --- | --- | --- | --- |
| | Maleate | Benzoate | Oxalate |
| 30° C./60% RH: 2 Weeks | O | O | Not Determined |
| Xenon: 26 Hours | O | E | E |
| Fluorescence: 5.5 Months | O | Not Determined | Not Determined |

Where: E≈presence of 2%–4% 1c. Maleate and benzoate salts were recrystallized from ethyl acetate and t-butyl methyl ether, respectively. Xenon exposure with the Atlas SunChex set for 0.4±0.1 watts/m². Fluorescent exposure with 1000-±100-ft candles. O=No E was detected.

Aqueous Solubility of Crystalline Salts of 1a

Compounds such as the muscarinic agonist 1a, which are intended for long-term oral administration usually display better systemic bioavailability following oral administration when they are readily soluble in water. Thus, water solubility is another key consideration in identifying a viable salt of 1a. As shown in Table VI, 1a maleate is about 15 times more soluble in water than 1a benzoate.

TABLE VI

| Aqueous Solubility of 1a Maleate and Benzoate Salts | | |
| --- | --- | --- |
| | Maleate | Benzoate |
| Water Solubility (mg/mL, room temp.) | 89 | 6 |

As evidenced by all the preceding data, the maleate salt of 1a is the only crystalline salt that meets all the criteria set forth for the optimal pharmaceutical development of 1a. While maleate salts are common in the field of pharmaceuticals, the finding that only the maleate salt of 1a, out of more than 25 salts evaluated, is the only salt with the desired physical and chemical properties to allow the pharmaceutical development of 1a is indeed an unexpected discovery.

DETAILED DESCRIPTION OF THE DRAWINGS

FIG. 1. Isomer Selective Assay

For analytical purposes, the separation of the Compound 1a from 1c was carried out with a 4.6-×250-mm Zorbax SBCN 5 - μm column (PN 880975.905) on an HP-1090 system with three solvent reservoirs. Conditions for separation were:

Mobile Phase:
 A=80%: 50 mMTEA adjusted to pH 3 with $H_3PO_4$.
 B=10%: $CH_3CN$.
 C=10%: MeOH.

Mobile Flow Rate: 1.5 mL/min

Temperature: RT

Injection Volume: 100 μL

Draw Speed: 83.3 μL/min

FIG. 1 shows a typical separation of a sample of 1a maleate containing some of 1c maleate. The first peak at 3.3 minutes is due to the counter-ion maleate while the peaks at 11.3 and 13.0 are due to 1a and 1c, respectively. These identifications were confirmed by NMR. The chromatogram shows a near equilibrium ratio of 1a to 1c of 85.5:14.5.

Figure 2:
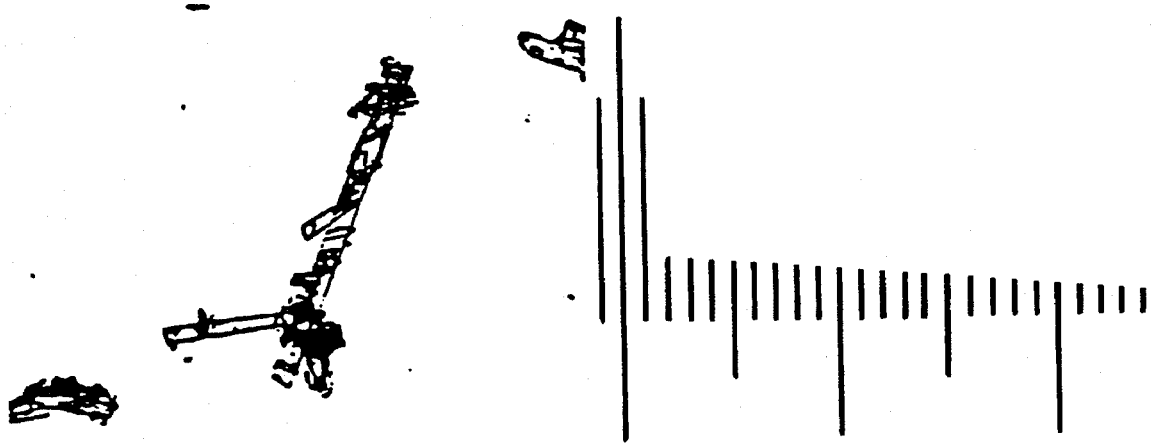
FIG. 2 shows an electron micrograph of 1a maleate crystals recrystallized from ethyl acetate.
Figure 3:
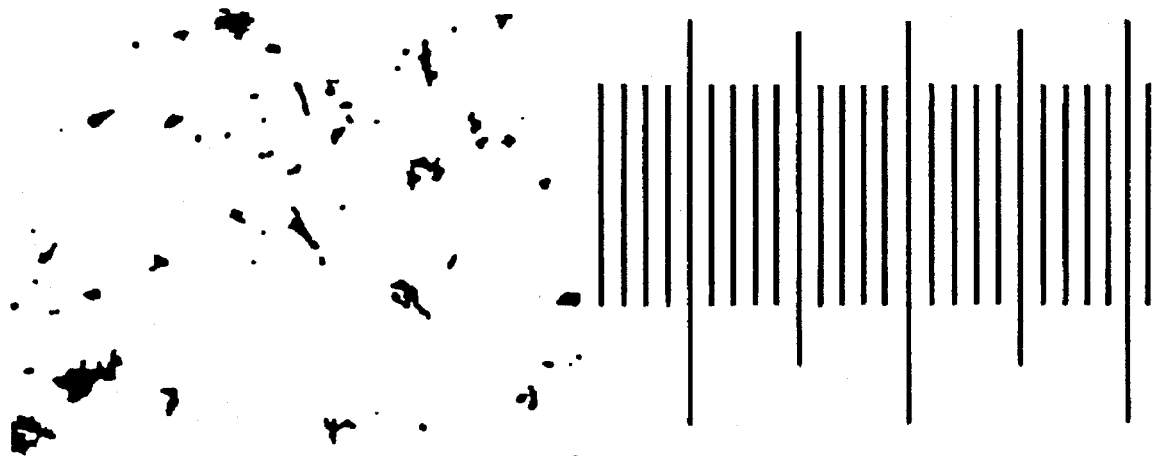
FIG. 3 shows an electron micrograph of 1a maleate crystals obtained by precipitation from diethyl ether.

FIGS. 2 and 3, Effect of Particle Size

FIGS. 2 and 3 show the order of magnitude difference in the particle size of an ethyl acetate recrystallized maleate salt of the compound (FIG. 2) versus the ether-precipitated product (FIG. 3). For FIG. 2, the range of particle sizes varied from 150×10 μm to less than 10×10 μm; for the ether-precipitated product in FIG. 3, all particles were less than 10×10 μm. This product was formed when the free base form of the compound in diethyl ether was mixed with maleic acid in diethyl ether. This type of in situ salt formation produced very fine particles due to rapid precipitation.

The ether-precipitated product (FIG. 3) was deliquescent and reverted to its equilibrium ratio of Z- to E-oxime (85% mZ-15%E) after 2 weeks at the accelerated stability condition, 40° C./75% RH. The ethyl acetate recrystallized product (FIG. 2) reported in Table II was more stable. This increased stability of the ethyl acetate crystallized form was most likely due to the relatively small total surface area of the larger recrystallized particles (FIG. 2) compared to the smaller precipitated particles (FIG. 3).

Figure 4:
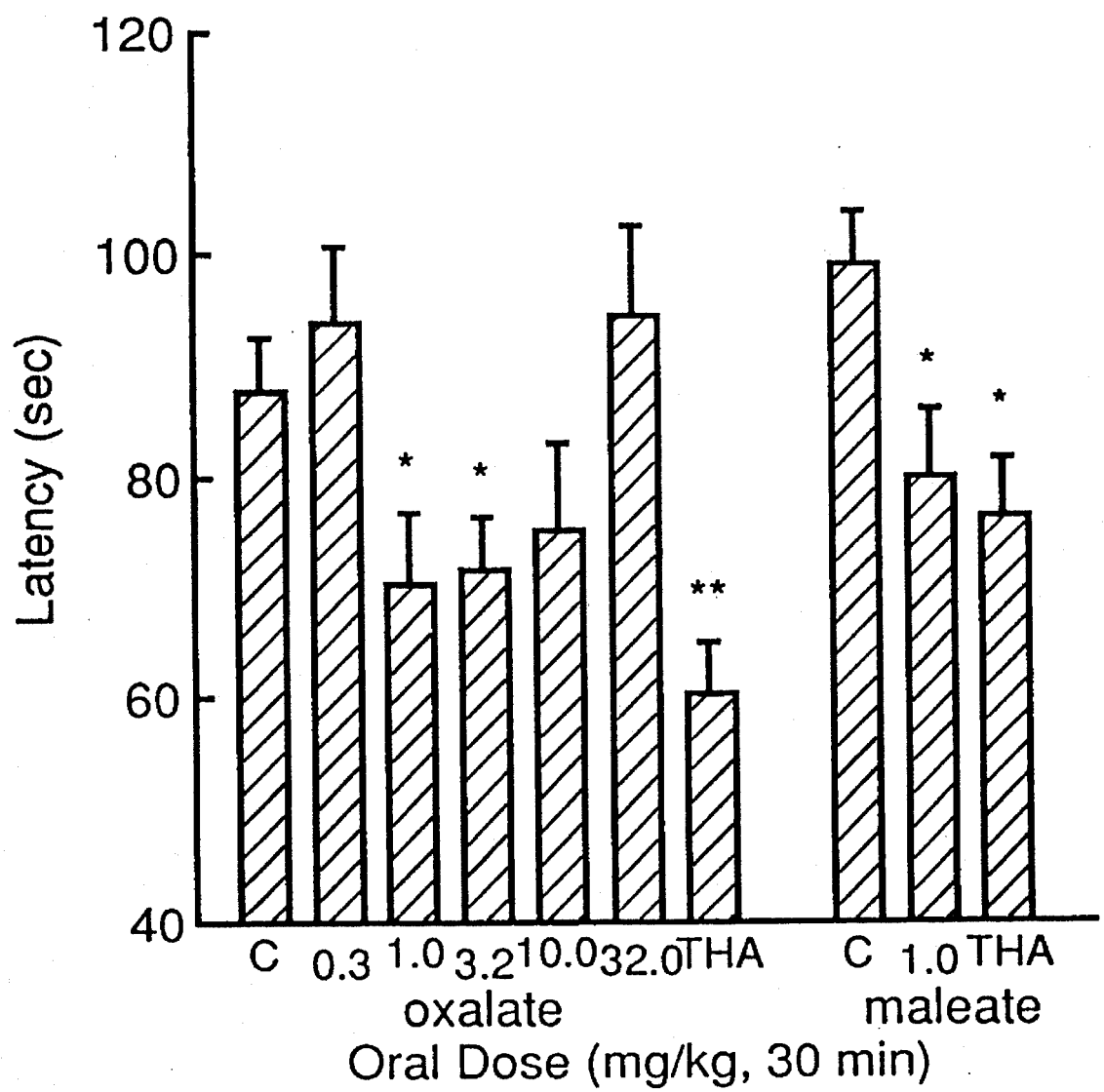
FIG. 4 shows a comparison of oxalate and maleate salts of 1a in biological activity.

FIG. 4, Biological Activity

FIG. 4 shows a comparison of the oxalate and maleate salts of 1a in their ability to improve the performance of hippocampally deficient mice in a mouse water maze test (see Jaen, et al., Life Sci ref. and refs. therein for more details on this test).

This test measures the ability of a compound to decrease the amount of time needed by the mice to find a hidden platform in the water pool.

The graph represents two sets of experiments, each one with its own control group. The data demonstrate that the oxalate salt of Compound 1a, which had been previously used to evaluate the effects of 1a in the mouse water maze test, can reduce the time required to find the platform by about 18 seconds (at 1 mg/kg). As a positive control, the acetylcholinesterase inhibitor tacrine (TEA) produced about a 27-second improvement. In a separate set of experiments, the maleate salt of 1a, at 1 mg/kg, produced about 20 seconds latency improvement, while the tacrine control group experienced a 24-second improvement. These data demonstrate that no loss of biological activity is experienced with the maleate salt of 1a, as compared to other salts that have been evaluated.

To assess the potential for the maleate salt of the compound to form polymorphs, crystallization was studied in five different solvent systems: isopropanol/ethanol/pentane, ethanol/pentane, ethanol, chloroform/pentane, and dichloromethane/pentane. The volume of solvent used, percent yield, mp before recrystallization, and mp after recrystallization are given in Table VI. For each of the experiments in Table VI, 1.0 g of maleate salt of oxime of the compound was dissolved under ambient conditions into the more polar of the solvents in the solvent system. This was followed by slow, incremental addition of pentane until small particulates could be observed. The mixture was then sealed and stored in the refrigerator overnight, followed by cold filtration, pentane rinse, and subjection to high-vacuum. All products are pure by both elemental and HPLC analyses. Powder x-ray diffraction studies on these lots were carried out and based on the data, the maleate salt of the compound crystallized in a variety of solvents showed the same diffraction pattern and the same crystal form. In general, solvents that allow the slow crystallization of the maleate salt lead to larger particle size material, which is more stable under accelerated stability conditions.

The maleate salt was, as discussed above, identified as significantly superior to all other salt forms considered.

TABLE VI

Room Temperature Recrystallizations

| Solvent System | Volume (mL/g) | % Yield | MP Before | MP After |
| --- | --- | --- | --- | --- |
| Isopropanol-Ethanol-Pentane | 202 | 77.2 | 116–119 | 116.5–118 |
| Ethanol-Pentane | 125 | 85.8 | 116–118 | 118.5–121 |
| Ethanol | 50 | 50.1 | 116–118 | 114–118 |
| Chloroform-Pentane | 32.5 | 83.1 | 116–118 | 118–119.5 |
| Dichloromethane-Pentane | 13 | 64.5 | 116–118 | 118–120 |

The preparation of 1a maleate can be achieved in a variety of ways. For example, the pure 1a isomer can be obtained by column chromatography of the approximately 1:1 mixture of 1a and 1c that is obtained synthetically (U.S. Pat. No. 5,306,718, U.S. Pat. No. 5,346,911, and Tecle, et al., *Bio. org. Med. Chem. Letters* 1995(5):631–636). The free base of 1a is typically obtained as an oil or oily solid. This free base can be stored refrigerated at –4° C. for up to several days without noticeable decomposition or isomerization to produce 1c. Preparation of the maleate salt typically involves the dissolution of 1a in an organic solvent and the addition of a solution of approximately one molar equivalent of maleic acid in the same solvent. Useful organic solvents for this purpose are, for example, ether solvents, such as diethyl ether, THF, and the like, ethyl acetate, isopropyl acetate and the like, alcohol solvents such as methanol, ethanol, isopropanol, and the like, hydrocarbon solvents such as hexane, benzene, toluene, and the like, and any other organic solvents that do not react with 1a. Preferred solvents include diethyl ether, ethyl acetate, and ethanol. Depending on the choice of solvent, the salt will precipitate immediately from the organic solvent (such as from diethyl ether), or may be recovered by subsequent addition of a second solvent (such as addition of diethyl ether or hexane to a solution of salt in ethanol) or by evaporation of the solvent under reduced pressure. The salts obtained by these procedures typically possess small particle size crystals. Since small particle size leads to increased hygroscopicity, the initial 1a maleate obtained can be recrystallized from an organic solvent or solvent mixtures, taking care of utilizing solvents that do not require heating to induce solubilization of the salt. Examples of useful solvents for this purpose include ethyl acetate, isopropanol, and diethyl ether, although other non-reactive solvents can be utilized, including water and mixtures of water with water-miscible organic solvents. Recrystallization temperatures are typically kept at or below room temperature, to minimize the possibility of oxime isomerization. In some cases, such as when using non-protic solvents such as ethyl acetate, the recrystallization temperature can be higher than room temperature.

Alternatively, mixtures of various ratios of 1a and 1c free bases can be converted to the corresponding mixtures of maleate salts, by procedures similar to those described above for pure 1a, and which can be recrystallized from organic or aqueous solvents or mixtures of solvents to yield pure 1a maleate. Solvents of choice for the recrystallization of 1a/1c maleate mixtures include, for example, isopropanol, ethanol, chloroform, dichloromethane, pentane, hexane, ethyl acetate, and the like.

The physical properties of 1a maleate influence its chemical stability. Deliquescence appears to be a major initiating event. However, particle size of the salt strongly influences deliquescence, due to the larger surface area for exposure to moisture in smaller particles. In addition, contamination of the higher melting point 1a maleate with the lower-melting 1c maleate facilitates deliquescence. Thus, increased stability of solid 1a maleate can be achieved by minimizing the presence of isomeric 1c as an impurity and by recrystallizing 1a maleate in such a way that ensures the production of large particle size crystals.

EXAMPLE 1

Preparation of [1:1]maleate salt of [R-(Z)]-1-azabicyclo[2.2.1]heptan-3-one, 0-[3-(3-methoxyphenyl)-2-propynyl]oxime Free base [R-(Z)]-1-azabicyclo [2.2.1]heptan-3-one, O-[3-(3-methoxyphenyl)-2-propynyl]oxime (1a) (6.8 g, 0.025 mol) was dissolved in ether. Some insoluble white solid was separated by filtration and discarded. Maleic acid (2.942 g, 0.025 mol) was dissolved in ether. The maleic acid solution was added dropwise into the ether solution of free base while stirring vigorously. The resulting precipitate was separated by filtration, dried in vacuo at 40° C. for 16 hours to give 8.93 g (92% yield) of 1a maleate, mp 116.5°–118.0° C.; [α]–10.7° (c=0.646, MeOH);

Mass Spectrum: m/z 272 (M+1), 271, 174, 145, 109, 99; IR (KBr): 2926, 2237, 1697, 1618, 1606, 1576, 1487, 1360, 1294, 1208, 1173, 1055, 1030, 916, 870, 779 cm$^{-1}$; $^1$H NMR (DMSO-d$_6$): δ7.31 (1H, t, J=7.7 Hz), 7.00 (m, 3H), 6.04 (s, 2H), 4.92 (s, 2H), 4.09 (dd, 2H, J=2.4 Hz, J=16.4 Mz), 3.76 (s, 3H), 3.52 (d, 1H, J=0.001), 3.36 (m, 6H), 2.24 (m, 1H), 1.75 (m, 1H); $^{13}$C NMR (DMSO-d$_6$): δ26.0, 51.6, 55.7, 55.8, 59.5, 62.4, 85.9, 86.3, 115.9, 116.8, 123.2, 124.4, 130.4, 136.0, 158.5, 159.6, 167.6;

Elemental analysis ($C_{16}H_{18}N_2O_2 \cdot C_4H_4O_4$) C, 62.17; H, 5.74; N, 7.25; Found: C, 61.97; H, 5.77; N, 7.15. HPLC Analysis: 100% 1a, RT=6.18 min (Column=Altech altima CN 4.5×150 cm, 5µ; Mobile phase=15% MeOH:AcCN (1:1) and 85% 50 mmol of $Et_3N$ in $H_2O$; 1.5 mL/min).

EXAMPLE 2

Recrystallization of 1a from Ethyl Acetate

The maleate salt of 1a (0.6297 g, 1.6 mmol) was dissolved in 13 mL boiling ethyl acetate. Upon cooling to room temperature, white crystals separated out. This was left in the refrigerator for 14 hours. The resulting white crystals were separated by filtration, dried under high vacuum at 50° C. yielding 0.528 g (84% recovery) of the recrystallized material, mp 118°–119° C.; HPLC, 99.8% 1a, 0.2% 1c (Column=Zorbax CN 4.5×250 cm, 5µ; Mobile phase=15% MeOH:AcCN (1:1) and 85% 50 mmol of $Et_3N$; 1.5 mL/min); [α]–9.5° (c=0.503, MeOH); MS m/z 272 ($M^{+1}$), 174, 145, 99, 82; IR (KBr): 2926, 2237, 1697, 1618, 1606, 1576, 1487, 1360, 1294, 1208, 1173, 1055, 1030, 916, 870, 779 $cm^{-1}$; $^1$H NMR (DMSO-$d_6$): δ7.31 (t, 1H, J=7.7 Hz), 7.00 (m, 3H), 6.04 (s, 2H), 4.92 (s, 2H), 4.09 (dd, 2H, J=2.4 Hz, J=16.4 Mz), 3.76 (s, 3H), 3.52 (d, 1H, J=0.01), 3.36 (m, 5H), 2.24 (m, 1H), 1.75 (m, 1H); $^{13}$C NMR (DMSO-$d_6$): 26.0, 51.6, 55.7, 55.8, 59.5, 62.4, 85.9, 86.3, 115.9, 116.8, 123.2, 124.3, 130.4, 136.1, 158.6, 159.5, 167.6.

Elemental analysis ($C_{16}H_{18}N_2O_2 \cdot C_4H_4O_4$): C, 62.17; H, 5.74; N, 7.25; Found: C, 61.98; H, 5.69; N, 7.14.

EXAMPLE 3

Room Temperature Recrystallization of 1a Maleate

The maleate salt of 1a (15.02 g) was dissolved in 800 mL of absolute ethanol with stirring under ambient conditions. Pentane (500 mL) was added in 100 mL increments until visual detection of crystallization. Precipitation of a white crystalline solid ensued rapidly. The mixture was diluted with an additional 600 mL of absolute ethanol with vigorous stirring until homogenous. Pentane (1.25 L) was added incrementally until visual detection of a few small crystals. The crystallization flask was sealed and stored in the freezer overnight.

The white crystals were collected by vacuum filtration and dried in a high-vacuum oven (ca. 10 mmHg; 40° C.) for 2 hours to afford 11.96 g (80% recovery) of 1a as a colorless crystalline solid; mp 118°–119° C. (dec). HPLC: 99.93% 1a: 0.07% 1c (Column=Altech altima CN 4.5×150 cm, 5µ; Mobile phase=15% MeOH:AcCN (1:1) and 85% 50 mmol of $Et_3N$ in $H_2O$; 1.5 mL/min); $^1$H-NMR (400 MHz; DMSO-$d_6$): δ7.31 (t, 1H, J=7.7 Hz), 7.04-7.00 (m, 2H), 6.99 (s, 1H), 6.06 (s, 2H), 4.93 (s, 2H), 4.19-4.03 (m, 2H), 3.77 (s, 3H), 3.52 (d, 1H, J=4.1 Hz), 3.45-3.29 (m, 4H), 2.27-2.20 (m, 1H), 1.78-172 (m, 1H) ppm; MS (CI) M+1=271; IR (KBr): 2926 (w), 2237 (w), 1697 (w), 1575 (s), 1360 (s), 1293 (m), 1207 (s), 1172 (m), 1054 (m), 1029 (m), 960 (w), 915 (m), 871 (m), 780 (m), 755 (w), 685 (w), 647 (w), 584 (w) $cm^{-1}$; $^{13}$C-NMR (100 MHz; DMSO-$d_6$): δ167.67, 159.60, 158.62, 136.19, 130.41, 124.37, 123.18, 116.82, 115.87, 86.33, 85.92, 62.40, 59.48, 55.79, 55.69, 51.58, 26.02 ppm.

Elemental analysis ($C_{16}H_{18}N_2O_2 \cdot C_4H_4O_4$): C, 62.17; H, 5.74; N, 7.25; Found: C, 62.27; H, 5.86; N, 7.23.

We claim:

1. (R)-(Z)-1-Azabicyclo[2.2.1]heptan-3-one,O-[3-(3-methoxyphenyl)-2-propynyl]oxime maleate as a pharmaceutical agent.

2. A compound according to claim 1 wherein the majority of crystal particles are greater than 10×10 µm in size.

3. A pharmaceutical composition useful for alleviating pain in a mammal comprising an analgesically effective amount of a compound according to claim 1 together with a pharmaceutically acceptable carrier.

4. A pharmaceutical composition useful for treating the symptoms of cognitive impairment comprising a therapeutically effective amount of a compound according to claim 1 together with a pharmaceutically acceptable carrier.

5. A method of alleviating pain in a mammal which comprises administering to said mammal a compound according to claim 1.

6. A method of treating the symptoms of cognitive impairment in a mammal which comprises administering to said mammal a compound according to claim 1.

* * * * *